United States Patent [19]

Sato et al.

[11] Patent Number: 5,159,082

[45] Date of Patent: Oct. 27, 1992

[54] PROCESS FOR PRODUCING AROMATIC COMPOUND

[75] Inventors: Keiichi Sato; Toru Okoshi, both of Tokyo, Japan

[73] Assignee: Mitsubishi Kasei Corporation, Tokyo, Japan

[21] Appl. No.: 542,549

[22] Filed: Jun. 25, 1990

[30] Foreign Application Priority Data

Jun. 24, 1989 [JP] Japan .................................. 1-162423

[51] Int. Cl.$^5$ .................. C07D 211/70; C07C 49/213; C07C 2/66; C07C 2/02
[52] U.S. Cl. .................................... 546/348; 558/301; 558/352; 558/91; 560/102; 568/309; 568/310; 568/331; 568/631; 568/747; 568/926; 570/129; 570/143; 570/188; 570/190; 570/202; 570/206; 585/425; 585/426
[58] Field of Search ......................... 546/348; 560/102; 566/631, 747, 928, 309, 310, 331; 585/426, 457, 466, 425, 438; 570/190, 129, 143, 188, 202, 206; 558/411, 357, 301

[56] References Cited

U.S. PATENT DOCUMENTS 4,879,060  11/1989  Shionozaki et al. ................. 541/348

FOREIGN PATENT DOCUMENTS 0206543  12/1986  European Pat. Off. .

OTHER PUBLICATIONS

Chemical Abstracts, vol. 76, No. 15, Apr. 10, 1972, p. 389, Abstract No. 85468a, Columbus, Ohio, U.S.; R. Selke et al.: "Diaryl formation and arylation of olefins by reactions of aryl sufinates and palladium salts", J. Prakt. Chem. 1971, 313(5), 875–881.
Patent Abstracts of Japan, vol. 13, No. 124 (C-580) [3472], Mar. 27, 1989; & JP-A-63 295 520 (Yuki Gosei Yakuhin Kogyo K.K.) Jan. 12, 1988.

*Primary Examiner*—C. Warren Ivy
*Assistant Examiner*—Raymond Covington
*Attorney, Agent, or Firm*—Sughrue, Mion, Zinn, Macpeak & Seas

[57] ABSTRACT

A process for producing an aromatic compound is disclosed, which comprises coupling an aromatic sulfinic acid or a salt thereof with an aromatic halogen compound having at least one halogen atom attached to the carbon atom of the aromatic nucleus thereof or a vinyl group-containing halogen compound having at least one halogen atom attached to the carbon atom of said vinyl group in the presence of a catalyst compound containing an element selected from platinum metals.

30 Claims, No Drawings

PROCESS FOR PRODUCING AROMATIC COMPOUND

FIELD OF THE INVENTION

The present invention relates to a novel process for producing an aromatic compound which comprises subjecting an aromatic sulfinic acid or a salt thereof and an aromatic halogen compound or a vinyl halogen compound to a $SO_2$-removal coupling reaction.

BACKGROUND OF THE INVENTION

Polycyclic aromatic compounds and aromatic vinyl compounds are useful materials as various industrial starting materials. Examples of conventional processes for producing polycyclic aromatic compounds include a process in which aromatic halogen compounds are dehalogenated and coupled in the presence of a palladium catalyst and carbon monoxide, as described in JP-A-61-293932 (the term "JP-A" as used herein means an "unexamined published Japanese patent application"); and a process in which a phenylmagnesium halide is coupled with a phenyl halide in the presence of nickel chloride, as described in JP-A-63-295520. Examples of conventional processes for producing aromatic vinyl compounds include a process in which an olefin and an aromatic compound are subjected to an oxidative coupling reaction in the presence of a palladium catalyst under oxygen pressure, as described in Sekiyu Gakkai-shi (Journal of the Petroleum Society), Vol. 15, No.2, page 91 (1972).

However, the process, in which aromatic halogen compounds are dehalogenated and coupled in the presence of a palladium catalyst and carbon monoxide, has a problem in that polycyclic compounds having an unsymmetrical structure can not be obtained. The process, in which a phenylmagnesium halide is coupled with a phenyl halide in the presence of nickel chloride, has a disadvantage in that the phenylmagnesium halide is difficult to handle. Further, the process, in which an olefin and an aromatic compound are subjected to an oxidative coupling reaction in the presence of a palladium catalyst under oxygen pressure, has disadvantages in that since the reaction is carried out under oxygen pressure, there is a danger of explosion and selectivity is poor.

SUMMARY OF THE INVENTION

An object of the present invention is to provide a novel process for producing a polycyclic aromatic compound and an aromatic vinyl compound with high selectivity in high yields by a coupling reaction.

Other objects and effects of the present invention will be apparent from the following description.

The above-described objects of the present invention can be easily achieved by a process comprising coupling an aromatic sulfinic acid or a salt thereof with an aromatic halogen compound having at least one halogen atom attached to the carbon atom of the aromatic nucleus thereof or a vinyl group-containing halogen compound having at least one halogen atom attached to the carbon atom of the vinyl group (vinyl halogen compound) in the presence of a catalyst compound containing an element selected from platinum group metals.

DETAILED DESCRIPTION OF THE INVENTION

The present invention will be illustrated in more detail below.

Examples of the aromatic sulfinic acid or salt thereof which can be used as a starting material in the present invention include conventional aromatic sulfinic acids and their salts such as ammonium salt, alkali salts, alkaline earth metal salts and zinc salt. Among them, alkali salts and alkaline earth metal salts are preferred, and alkali metal salts such as sodium salt, lithium salt and potassium salt are particularly preferred.

Examples of the aromatic nucleuses of these aromatic sulfinic acids include a benzene ring, a biphenyl ring, a condensed ring such as a naphthalene ring, and a heterocyclic ring such as a pyridine ring. These aromatic nucleuses may have one or more substituents which do not have an adverse effect on the coupling reaction. In general, the nucleus has three or less of these substituents. Examples of the substituents include an alkyl group, an alkoxy group, a halogen atom, an amino group, a nitro group, an acetylamino group, a phenyl group, a carboxyl group and salts thereof and a —$SO_2H$ group and salts thereof. There is no particular limitation with regard to positions to which these substituents are attached.

Examples of the aromatic sulfinic acids and salts thereof include benzenesulfinic acid, alkylbenzene sulfinic acids having an alkyl group having 1 to 13 carbon atoms, xylenesulfinic acid, trimethylbenzenesulfinic acid, alkoxybenzenesulfinic acids having an alkoxy group having 1 to 13 carbon atoms, fluorobenzenesulfinic acid, chlorobenzenesulfinic acid, bromobenzenesulfinic acid, aminobenzenesulfinic acid, nitrobenzenesulfinic acid, acetylaminobenzenesulfinic acid, carboxybenzenesulfinic acid, dicarboxybenzenesulfinic acid, naphthalenedisulfinic acid, benzenedisulfinic acid, and biphenyldisulfinic acid and salts thereof. However, the aromatic sulfinic acids and salts thereof are not limited to the above-described compounds and other sulfinic acid compounds may be used in the present invention.

Examples of the halogen atom of the aromatic halogen compound having at least one halogen atom attached to carbon atom of the aromatic nucleus or the vinyl halogen compound which can be used as other starting material in the present invention include a chlorine atom, a bromine atom and an iodine atom. Examples of the aromatic nucleus of the aromatic halogen compound include a benzene ring, a biphenyl ring, a condensed ring such as a naphthalene ring, and a heterocyclic ring such as a pyridine ring. These aromatic nucleuses may have one or more substituents which do not have an adverse effect on the coupling reaction. In general, the nucleus has three or less of these substituents. Examples of these substituents include an alkyl group, an alkoxy group, a hydroxy group, an amino group, a nitro group, an acetylamino group, a cyano group, an acyl group, an alkoxycarbonyl group, and a carboxyl group and salts thereof. There is no particular limitation with regard to positions at which these substituents are attached.

The vinyl halogen compound can be represented by the following formula:

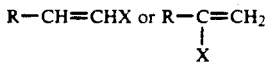

wherein X represents a halogen atom and R represents hydrogen atom, an alkyl group or a phenyl group.

Examples of the aromatic halogen compound and the vinyl halogen compound which can be used in the present invention include chlorobenzene, bromobenzene, iodobenzene, dichlorobenzene, dibromobenzene, chlorofluorobenzene, bromofluorobenzene, bromochlorobenzene, chloroalkylbenzenes having an alkyl group having 1 to 13 carbon atoms, bromoalkylbenzenes having an alkyl group having 1 to 13 carbon atoms, chloroxylene, bromoxylene, chlorotrimethylbenzene, bromotrimethylbenzene, chloroalkoxybenzenes having an alkoxy group having 1 to 13 carbon atoms, bromoalkoxybenzenes having an alkoxy group having 1 to 13 carbon atoms, chlorophenol, bromophenol, chloroaniline, bromoaniline, chloronitrobenzene, bromonitrobenzene, dimethyl chlorophthalate, dimethyl bromophthalate, chloroacetanilide, bromoacetanilide, chlorobenzonitrile, bromobenzonitrile, chloroacetophenone, bromoacetophenone, methyl chlorobenzoate, methyl bromobenzoate, chlorobenzoic acid, bromobenzoic acid, alkali salts or alkaline earth metal salts of chlorobenzoic acid, alkali salts or alkaline earth metal salts of bromobenzoic acid, dimethyl chlorobenzene-dicarboxylate, dimethyl bromobenzenedicarboxylate, chlorobenzenedicarboxylic acid, bromobenzenedicarboxylic acid, alkali salts or alkaline earth metal salts of chlorobenzenedicarboxylic acid, alkali salts or alkaline earth metal salts of bromobenzenedicarboxylic acid, chloronaphthalene, bromonaphthalene, bromobiphenyl, dibromobiphenyl, bromoanthracene, chloropyridine, bromopyridine, vinyl chloride, vinyl bromide, β-bromostyrene, 1-chloropropylene, 2-chloropropylene, 1-bromopropylene and 2-bromopropylene. However, the aromatic halogen compounds and the vinyl halogen compounds are not limited to the above-described compounds and other compounds may be used in the present invention.

The coupling reaction of the present invention can be carried out by dissolving the aromatic sulfinic acid or a salt thereof and the aromatic halogen compound or the vinyl halogen compound in a solvent, and then heating the resulting solution in the presence of a catalyst compound containing an element selected from platinum group metals.

Examples of platinum group metals which can be contained in the catalyst compound of the present invention include Pd, Os, Ir, Pt, Ru and Rh. Preferred examples thereof include metals such as Pd, Ir, Pt and Rh. Catalyst compounds containing Pd are particularly preferred.

Examples of the catalyst compound containing these elements selected from platinum group metals include metallic powders such a palladium black; catalysts supported on a carrier (e.g., activated carbon or alumina) such as palladium supported on activated carbon and palladium supported on alumina; halides such as palladium chloride, palladium bromide and palladium iodide; salts of inorganic acids such as nitrates (e.g., palladium nitrate), sulfates (e.g., palladium sulfate) and sodium tetrachloropalladate; salts of organic acids such as acetates (e.g., palladium acetate) and benzoates (e.g., palladium benzoate); chelate salts containing β-diketones such as acetylacetone (e.g., palladium acetylacetone); metal 0-valent complexes such as tetrakis(triphenylphosphine)palladium; and organometallic compounds such as dichloro(1,5-cyclo-octadiene)palladium.

Compounds having an organophosphorus compound as a ligand are particularly preferred. Examples of the organophosphorus compound ligand include triphenylphosphine; bis(diphenylphosphino)straight-chained or branched alkane such as 1,2-bis(diphenylphosphino)ethane, 1,3-bis(diphenylphosphino)propane, 1,4-bis(diphenylphosphino)butane, 1,5-bis(diphenylphosphino)pentane and 1,6-bis(diphenylphosphino)hexane; 1,1'-bis(diphenylphosphino)ferrocene; 1,2-(diphenylphosphinomethyl)cyclobutane; bis(α,α'-diphenylphosphino)-o-xylene; tributylphosphine and trioctylphosphine.

If desired, the catalyst compounds containing elements selected from platinum group metals may be used in combination with organophosphorus compounds capable of being converted to organophosphorus compound ligands instead of using the catalyst compounds containing elements selected from platinum group metals and having the organophosphorus compound ligands. Examples of the organophosphorus compounds include those already described above for the organophosphorus compound ligands.

As the solvent, any of solvents which can be dissolve the starting materials can be used. Examples of the solvents include polar solvents such as nitrogen-containing compounds, sulfur-containing compounds and phosphorous-containing compounds. More specifically, examples of the solvents include N,N-dimethylformamide, N,N-dimethylacetamide, N-methyl-2-pyrrolidone, dimethyl sulfoxide, sulfolane and hexamethylphosphoric triamide. These solvents may be used either alone or as a mixture of two or more of them.

With regard to the ratio of each starting materials and components to be used, the aromatic sulfinic acid or a salt thereof is preferably used in an amount of 0.1 to 10 mol, more preferably 0.5 to 3 mol, per mol of the aromatic halogen compound or the vinyl halogen compound. The catalyst compound is preferably used in an amount of 0.0001 to 1 mol, more preferably 0.001 to 0.1 mol per mol of the aromatic halogen compound or the vinyl halogen compound. When the organophosphorus compound which can be converted into the organophosphorus compound ligand is used, the compound in an amount of 0.01 to 25 mol, more preferably 1 to 10 mol per mol of the catalyst compound is preferably added to the reaction mixture.

The reaction temperature is preferably 60° to 200° C., and more preferably 100° to 180° C.

Generally, the reaction is completed in a period of several hours, but the reaction time varies depending on reaction conditions such as reaction temperature, the amount of the catalyst compound, etc. The reaction may be carried out in air, but it is preferred that the reaction is carried out in an inert gas atmosphere such as nitrogen or argon gas.

It is preferred that a compound capable of trapping $SO_2$ formed by the reaction is allowed to exist in the reaction system. Examples of such compound for use in trapping $SO_2$ include oxides, hydroxides and carbonates of alkali earth metals such as magnesium oxide, calcium oxide, calcium hydroxide and calcium carbonate; zinc oxide; oxides, hydroxides, carbonates and silicates of alkaline metals such as lithium oxide, sodium hydroxide, potassium hydroxide, sodium carbonate, potassium carbonate and sodium silicate; and alkylamines such as triethylamine, tributylamine and trioctylamine. Among them, it is preferred to use oxides and hydroxides of alkali earth metals. Particularly preferred are calcium oxide and calcium hydroxide. Although there is no specific limitation with regard to the amount of these compound to be used, they are generally used in an amount of 0.1 to 100 times by mol the amount of the aromatic sulfinic acid or a salt thereof.

The process of the present invention can be carried out by any of batch processes, semi-batch processes and continuous processes.

The catalyst compound containing an element of platinum group metals can be separated and recovered from the reaction mixture by conventional methods such as extraction, crystallization or reduction method.

The aromatic compounds obtained by the process of the present invention can be separated and recovered from the reaction mixture by evaporation, distillation, crystallization or acid precipitation method according to the physical properties of the aromatic compounds.

The present invention is illustrated in greater detail by reference to the following examples which, however, are not to be construed as limiting the invention in any way, so long as they are not departed from the spirit and scope thereof.

EXAMPLE 1

3.56 g (20 mmol) of sodium p-toluenesulfinate, 3.42 g (20 mmol) of p-bromotoluene, 0.0225 g (0.1 mmol) of palladium acetate, 0.0478 g (0.12 mmol) of 1,2-bis(diphenylphosphino)-ethane, 6.73 g (120 mmol) of calcium oxide and 60 ml of N-methyl-2-pyrrolidone were placed in a 100 ml round bottom flask and reacted at 150° C. in a nitrogen gas stream for 8 hours. After the completion of the reaction, the reaction mixture was analyzed by means of high performance liquid chromatography. The analysis showed that 17.1 mmol (yield: 86%) of 4,4'-dimethylbiphenyl was formed in the reaction mixture solution.

EXAMPLE 2

3.56 g (20 mmol) of sodium p-tolunesulfinate, 2.75 g (20 mmol) of p-chlorobenzonitrile, 0.0225 g (0.1 mmol) of palladium acetate, 0.0478 g (0.12 mmol) of 1,2-bis(diphenylphosphino) ethane, 11.2 g (200 mmol) of calcium oxide and 60 ml of N-methyl-2-pyrrolidone were placed in a 100 ml round bottom flask and reacted at 150° C. in a nitrogen gas stream for 6 hours. After the completion of the reaction, the reaction mixture solution was analyzed by means of high performance liquid chromatography. The analysis showed that 4.9 mmol (yield 25%) of 4'-cyano-4-methyl-biphenyl was formed in the reaction mixture solution.

EXAMPLE 3

3.56 g (20 mmol) of sodium p-toluenesulfinate, 3.74 g (20 mmol) of p-bromoanisole, 0.0225 g (0.1 mmol) of palladium acetate, 0.0478 g (0.12 mmol) of 1,2-bis(diphenylphosphino)-ethane, 6.73 g (120 mmol) of calcium oxide and 60 ml of N-methyl-2-pyrrolidone were placed in a 100 ml round bottom flask and reacted at 150° C. in a nitrogen gas stream for 6 hours. After the completion of the reaction, the reaction mixture was analyzed by means of high performance liquid chromatography. The analysis showed that 15.0 mmol (yield 75%) of 4'-methoxy-4-methylbiphenyl was formed in the reaction mixture solution.

EXAMPLE 4

3.56 g (20 mmol) of sodium p-toluenesulfinate, 2.85 g (20 mmol) of chloroanisole, 0.0225 g (0.1 mmol) of palladium acetate, 0.0478 g (0.12 mmol) of 1,2-bis(diphenylphosphino)-ethane, 3.37 g (60 mmol) calcium oxide and 60 ml of N-methyl-2-pyrrolidone were placed in a 100 ml round bottom flask and reacted at 150° C. in a nitrogen gas stream for 6 hours. After the completion of the reaction, the reaction mixture was analyzed by means to high performance liquid chromatography. The analysis showed that 46% of sodium p-toluenesulfinate was converted and 8.5 mmol (yield 42%) of 4'-methoxy-4-methylbiphenyl was formed in the reaction mixture solution.

EXAMPLE 5

4.28 g (20 mmol) of sodium 1-naphthalenesulfinate, 4.14 g (20 mmol) of 1-bromonaphthalene, 0.0225 g (0.1 mmol) of palladium acetate, 0.0478 g (0.12 mmol) of 1,2-bis(diphenylphosphino)ethane, 6.73 g (120 mmol) of calcium oxide and 60 ml of N-methyl-2-pyrrolidone were placed in a 100 ml round bottom flask and reacted at 150° C. in a nitrogen gas stream for 8 hours. After the completion of the reaction, the reaction mixture was analyzed by means of high performance liquid chromatography. The analysis showed that 12.8 mmol (yield 64%) of 1,1'-binaphthyl was formed in the reaction mixture solution.

EXAMPLE 6

7.77 g (40 mmol) of solution p-methoxybenzenesulfinate, 7.14 g (40 mmol) of sodium p-chlorobenzoate, 0.0449 g (0.2 mmol) of palladium acetate, 0.0956 g (0.24 mmol) of 1,2-bis(diphenylphosphino)ethane, 22.4 g (400 mmol) of calcium oxide and 120 ml of N-methyl-2-pyrrolidone were placed in a 200 ml round bottom flask and reacted at 150° C. in a nitrogen gas stream for 8 hours. The reaction mixture was diluted with 250 ml of toluene and filtered to obtain a solid containing the salt of 4'-methoxybiphenyl-4-carboxylic acid together with calcium compounds resulted from trapping $SO_2$. While stirring the solid in 200 ml of water, 170 ml of concentrated hydrochloric acid was added portionwise thereto, whereby 4'-methoxybiphenyl-4-carboxylic acid was precipitated with evolution of sulfurous acid gas. The precipitate was recovered by filtration, washed with water and dried in vacuo to obtain 8.32 (36.5 mmol, yield 91%), of 4'-methoxybiphenyl-4-carboxylic acid.

8.32 g of 4'-methoxybiphenyl-4-carboxylic acid obtained was refluxed together with 100 ml of 48% hydrobromic acid and 200 ml of acetic acid for 14 hours. The reaction mixture was poured into 1 liter of water, whereby 4'-hydroxybiphenyl-4-carboxylic acid was precipitated out. The precipitate was recovered by filtration, washed with water and dried under reduced pressure to obtain 7.29 g (34.0 mmol, over-all yield 85%) of 4'-hydroxybiphenyl-4-carboxylic acid.

EXAMPLE 7

3.28 g (20 mmol) of sodium benzenesulfinate, 2.36 g (10 mmol) of o-dibromobenzene, 0.0255 g (0.1 mmol) of palladium acetate, 0.0478 g (0.12 mmol) of 1,2-bis(diphenylphosphino)-ethane, 6.73 g (120 mmol) of calcium oxide and 60 ml of N-methyl-2-pyrrolidone were placed in a 100 ml round bottom flask and reacted at 150° C. in a nitrogen gas stream for 8 hours. After the completion of the reaction, the reaction mixture was analyzed by means of high performance liquid chromatography. The analysis showed that 4.5 mmol (yield 45%) of o-terphenyl was formed in the reaction mixture solution.

EXAMPLES 8 TO 11

3.56 g (20 mmol) of sodium p-toluenesulfinate, 3.14 g (20 mmol) of bromobenzene, 0.0225 g (0.1 mmol) of palladium acetate, 0.0478 g (0.12 mmol) of 1,2-bis(diphenylphosphino)-ethane, 11.2 g (200 mmol) of calcium oxide and 60 ml of each solvent indicated in Table 1 were placed in a 100 ml round bottom flask and reacted at 150° C. in a nitrogen gas stream for 6 hours, respectively. After the completion of the reaction, the amount of 4-methyl-biphenyl formed was analyzed by means of high performance liquid chromatography. The results are shown in Table 1.

TABLE 1

| Ex. | Solvent | Yield of 4-methylbiphenyl |
|---|---|---|
| 8 | N-methyl-2-pyrrolidone | 17.5 mmol (88%) |
| 9 | dimethyl sulfoxide | 12.2 mmol (61%) |
| 10 | hexamethylphosphoric triamide | 8.5 mmol (43%) |

EXAMPLES 11 TO 13

3.56 g (20 mmol) of sodium p-toluenesulfinate, 3.14 g (20 mmol) of bromobenzene, 11.2 g (200 mmol) of calcium oxide, 60 ml of N-methyl-2-pyrrolidone and each catalyst compound and each organophosphorus compound ligand indicated in Table 2 were placed in 100 ml round bottom flask and reacted at 150° C. in a nitrogen gas stream for 6 hours, respectively. After the completion of the reaction, the amount of 4-methylbiphenyl formed was analyzed by means of high performance liquid chromatography. The results are shown in Table 2.

TABLE 2

| Ex. | Catalyst compound (amount) | Ligand (amount) | Yield of 4-methylbiphenyl |
|---|---|---|---|
| 11 | Palladium acetate 0.0225 g | triphenylphosphine 0.063 g | 17.6 mmol (88%) |
| 12 | Palladium acetate 0.0225 g | None | 17.0 mmol (85%) |
| 13 | 2% Pd/Al₂O 0.532 g | None | 14.8 mmol (74%) |

EXAMPLES 14 AND 15

3.56 g (20 mmol) of sodium p-toluenesulfinate, 3.14 g (20 mmol) of bromobenzene, 0.0225 g (0.1 mmol) of palladium acetate, 0.0478 g (0.12 mmol) of 1,2-bis(diphenylphosphino)-ethane, 60 ml of N-methyl-2-2pyrrolidone and each compound given in Table 3 were placed in a 100 ml round bottom flask and reacted at 150° C. in a nitrogen gas stream for 6 hours. After the completion of the reaction, the amount of 4-methylbiphenyl formed was analyzed by means of high performance liquid chromatography. The results are shown in Table 3.

TABLE 3

| Ex. | Compound (amount) | Yield of 4-methylbiphenyl |
|---|---|---|
| 14 | magnesium oxide | 11.8 mmol |

TABLE 3-continued

| Ex. | Compound (amount) | Yield of 4-methylbiphenyl |
|---|---|---|
|  | 8.07 g | (59%) |
| 15 | sodium carbonate 21.2 g | 9.7 mmol (49%) |

EXAMPLES 16 TO 26

3.28 g (20 mmol) of sodium benzenesulfinate, 0.0225 g (0.1 mmol) of palladium acetate, 0.0478 g (0.12 mmol) of 1,2-bis(diphenylphosphino)ethane, 6.73 g (120 mmol) of calcium oxide, 60 ml of N-methyl-2-pyrrolidone and 20 mmol of each halogen compound indicated in Table 4 were placed in a 100 ml round bottom flask and reacted at 150° C. in a nitrogen gas stream for 8 hours, respectively. After the completion of the reaction, the product was analyzed by means of high performance liquid chromatography. The results are shown in Table 4.

TABLE 4

| Ex. | Halogen compound | Product and yield |
|---|---|---|
| 16 | m-bromotoluene | 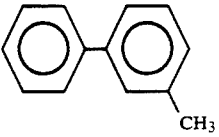 12.1 mmol (61%) |
| 17 | p-bromofluorobenzene | 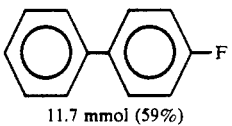 11.7 mmol (59%) |
| 18 | 4-bromobiphenyl | 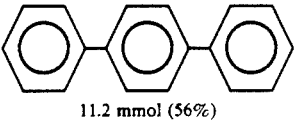 11.2 mmol (56%) |
| 19 | p-chloroacetophenone | 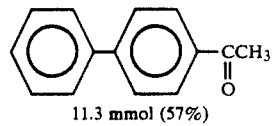 11.3 mmol (57%) |
| 20 | methyl p-chlorobenzoate | 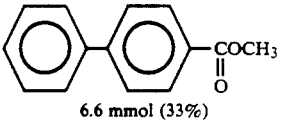 6.6 mmol (33%) |
| 21 | sodium p-bromobenzoate | 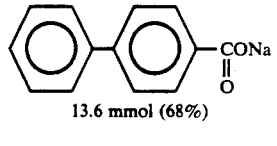 13.6 mmol (68%) |
| 22 | p-bromophenol | 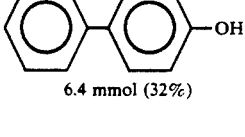 6.4 mmol (32%) |

TABLE 4-continued

| Ex. | Halogen compound | Product and yield |
|---|---|---|
| 23 | α-bromonaphthalene | 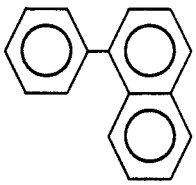<br>12.0 mmol (60%) |
| 24 | 9-bromoanthracene | 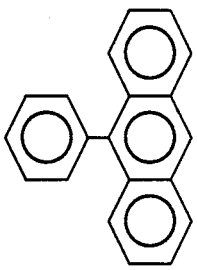<br>17.3 mmol (87%) |
| 25 | 3-bromopyridine | 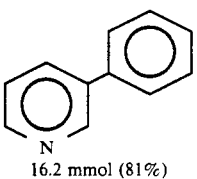<br>16.2 mmol (81%) |
| 26 | β-bromostyrene | 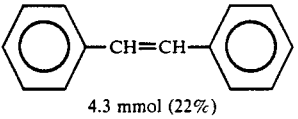<br>4.3 mmol (22%) |

COMPARATIVE EXAMPLE 1

2.88 g (20 mmol) of sodium n-butane sulfinate, 3.14 g (20 mmol) of bromobenzene, 0.0225 g (0.1 mmol) of palladium acetate, 0.0478 g (0.12 mmol) of 1,2-bis(diphenylphosphino)-ethane, 6.73 g (120 mmol) of calcium oxide and 60 ml of N-methyl-2-pyrrolidone were placed in a 100 ml round bottom flask and reacted at 150° C. in a nitrogen gas stream for 8 hours. After the completion of the reaction, the reaction product was analyzed by high performance liquid chromatography. n-Butylbenzene was not detected.

COMPARATIVE EXAMPLE 2

3.56 g (20 mmol) of sodium p-toluensulfinate, 2.81 g (20 mmol) of α-chloro-p-xylene, 0.0225 g (0.1 mmol) of palladium acetate, 0.0478 g (0.12 mmol) of 1,2-bis(diphenylphosphine) ethane, 6.73 g (120 mmol) of calcium oxide and 60 ml of N-methyl-2-pyrrolidone were placed in a 100 ml round bottom flask and reacted t 150° C. in a nitrogen gas stream for 6 hours. After the completion of the reaction, the reaction product was analyzed by means of high performance liquid chromatography. 4,4'-dimethyl-diphenylmethane was not detected.

While the present invention has been described in detail and with reference to specific embodiments thereof, it is apparent to one skilled in the art that various changes and modifications can be made therein without departing from the spirit and the scope of the present invention.

What is claimed is:

1. A process for producing an aromatic compound which comprises coupling an aromatic sulfinic acid or a salt thereof with an aromatic halogen compound having at least one halogen atom attached to the carbon atom of the aromatic nucleus thereof or a vinyl group-containing halogen compound having at least one halogen atom attached to the carbon atom of said vinyl group in the presence of a catalytically effective amount of a catalyst compound containing an element selected from platinum group metals, wherein said aromatic sulfinic acid or a salt thereof is used in an amount of 0.1 to 10 mol per mol of the aromatic halogen compound or the vinyl group-containing halogen compound.

2. A process for producing an aromatic compound as claimed in claim 1, wherein an aromatic sulfinic acid or a salt thereof is coupled with an aromatic halogen compound having at least one halogen atom attached to the carbon atom of the aromatic nucleus thereof in the presence of a catalyst compound containing an element selected from platinum group metals.

3. A process for producing an aromatic compound as claimed in claim 1, wherein an aromatic sulfinic acid or a salt thereof is coupled with a vinyl group-containing halogen compound having at least one halogen atom attached to the carbon atom of said vinyl group in the presence of a catalyst compound containing an element selected from platinum group metals.

4. A process for producing an aromatic compound as claimed in claim 1, wherein said aromatic sulfinic acid or a salt thereof is a compound having an aromatic nucleus selected from the group consisting of a benzene ring, a biphenyl ring, a naphthalene ring and a pyridine ring and said aromatic nucleus may be substituted.

5. A process for producing an aromatic compound as claimed in claim 1, wherein said salt of the aromatic sulfinic acid is an ammonium salt, an alkali salt, an alkaline earth metal salt or a zinc salt.

6. A process for producing an aromatic compound as claimed in claim 5, wherein said salt of the aromatic sulfinic acid is an alkali salt or an alkaline earth metal salt.

7. A process for producing an aromatic compound as claimed in claim 6, wherein said salt of the aromatic sulfinic acid is an alkali salt.

8. A process for producing an aromatic compound as claimed in claim 4, wherein said aromatic sulfinic acid or a salt thereof is a compound or a salt thereof selected from the group consisting of benzenesulfinic acid, an alkylbenzenesulfinic acid having an alkyl group having 1 to 13 carbon atoms, xylenesulfinic acid, trimethylbenzenesulfinic acid, an alkoxybenzenesulfinic acid having an alkoxy group having 1 to 13 carbon atoms, fluorobenzenesulfinic acid, chlorobenzenesulfinic acid, bromobenzenesulfinic acid, aminobenzenesulfinic acid, nitrobenzenesulfinic acid, acetylaminobenzenesulfinic acid, carboxybenzenesulfinic acid, dicarboxybenzenesulfinic acids naphthalenesulfinic acid, benzenedisulfinic acid, biphenyldisulfinic acid and salts thereof.

9. A process for producing an aromatic compound as claimed in claim 1, wherein said aromatic nucleus to which the halogen atom of the aromatic halogen compound is attached is a benzene ring, a biphenyl ring, a naphthalene ring or a pyridine ring.

10. A process for producing an aromatic compound as claimed in claim 9, wherein said aromatic halogen compound is a compound selected from the group consisting of chlorobenzene, bromobenzene, iodobenzene, dichlorobenzene, dibromobenzene, chlorofluorobenzene, bromofluorobenzene, bromochlorobenzene, a chloroalkylbenzene having an alkyl group having 1 to 13 carbon atoms, a bromoalkylbenzene having an alkyl group having 1 to 13 carbon atoms, chloroxylene, bromoxylene, chlorotrimethylbenzene, bromotrimethylbenzene, a chloroalkoxybenzene having an alkoxy group having 1 to 13 carbon atoms, a bromoalkoxybenzene having an alkoxy group having 1 to 13 carbon atoms, chlorophenol, bromophenol, chloroaniline, bromoaniline, chloronitrobenzene, bromonitrobenzene, chloroacetanilide, bromoacetanilide, dimethyl chlorophthalate, dimethyl bromophthalate, chlorobenzonitrile, bromobenzonitrile, chloroacetophenone, bromoacetophenone, methyl chlorobenzoate, methyl bromobenzoate, chlorobenzoic acid, bromobenzoic acid, an alkali salt or alkaline earth metal salt of chlorobenzoic acid, an alkali salt or alkaline earth metal salt of bromobenzoic acid, dimethyl chlorobenzenedicarboxylate, dimethyl bromobenzenedicarboxylate, chlorobenzenedicarboxylic acid, bromobenzenedicarboxylic acid, an alkali salt or alkaline earth metal salt of chlorobenzenedicarboxylic acid, an alkali salt or alkaline earth metal salt of bromobenzenedicarboxylic acid, chloronaphthalene, bromonaphthalene, bromobiphenyl, dibromobiphenyl, bromoanthracene, chloropyridine and bromopyridine.

11. A process for producing an aromatic compound as claimed in claim 1, wherein said vinyl group-containing halogen compound is a compound represented by the following formula:

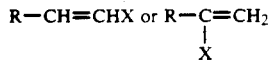

wherein X represents a halogen atom and R represents a hydrogen atom, an alkyl group or a phenyl group.

12. A process for producing an aromatic compound as claimed in claim 11, wherein said vinyl group-containing halogen compound is a compound selected from the group consisting of vinyl chloride, vinyl bromide, β-bromostyrene, 1-chloropropylene, 2-chloropropylene, 1-bromopropylene and 2-bromopropylene.

13. A process for producing an aromatic compound as claimed in claim 1, wherein said coupling reaction is carried out by dissolving the aromatic sulfinic acid or a salt thereof and the aromatic halogen compound or the vinyl group-containing halogen compound in a solvent, and then heating the resulting solution in the presence of a catalyst compound containing an element selected from platinum group metals.

14. A process for producing an aromatic compound as claimed in claim 1, wherein said element of platinum group metals is selected from the group consisting of Pd, Os, Ir, Pt, Ru, and Rh.

15. A process for producing an aromatic compound as claimed in claim 1, wherein said element of platinum group metals is Pd.

16. A process for producing an aromatic compound as claimed in claim 1, wherein said catalyst compound containing an element of platinum group metals is metallic powder, a catalyst supported on a carrier, a halide, a salt of an inorganic or organic acid, a chelate salt, a metal 0-valent complex or an organometallic compound.

17. A process for producing an aromatic compound as claimed in claim 1, wherein said catalyst compound is a compound having an organophosphorus compound as a ligand, or is used in combination with organophosphorous compounds capable of being converted to organophosphorous compound ligands.

18. A process for producing an aromatic compound as claimed in claim 17, wherein said organophosphorus compound ligand is triphenylphosphine, 1,2-bis(diphenylphosphino)-ethane, 1,3-bis(diphenylphosphino)-propane, 1,4-bis(diphenylphosphino)butane, 1,5-bis(diphenylphosphino)pentane, 1,6-bis(diphenylphosphino)hexane, 1,1'-bis(diphenylphosphino)ferrocene, 1,2-bis(diphenylphosphino methyl)cyclobutane, bis-(α,α'-diphenylphosphino)-o-xylene, tributylphosphine or trioctylphosphine.

19. A process for producing an aromatic compound as claimed in claim 13, wherein said solvent is solvent capable of dissolving the starting materials of the aromatic sulfinic acid or a salt thereof, the aromatic halogen compound and the vinyl group-containing halogen compound, and is a polar solvent selected from the group consisting of nitrogen-containing compounds, sulfur-containing compounds and phosphorus-containing compounds.

20. A process for producing an aromatic compound as claimed in claim 19, wherein said solvent is at least one compound selected from the group consisting of N,N-dimethylformamide, N,N-dimethylacetamide, N-methyl-2-pyrrolidone, dimethyl sulfoxide, sulfolane and hexamethylphosphoric triamide.

21. A process for producing an aromatic compound as claimed in claim 1, wherein said catalyst compound is used in an amount of 0.0001 to 1 mol per mol of the aromatic halogen compound or the vinyl group-containing halogen compound.

22. A process for producing an aromatic compound as claimed in claim 17, wherein said organophosphorus compound is used in an amount of 0.01 to 25 mol per mol of the catalyst compound.

23. A process for producing an aromatic compound as claimed in claim 1, wherein said coupling reaction is carried out at a temperature of 60° to 200° C.

24. A process for producing an aromatic compound as claimed in claim 1, wherein said coupling reaction is carried out in an inert gas atmosphere.

25. A process for producing an aromatic compound as claimed in claim 1, wherein a compound capable of trapping SO₂ formed by the coupling reaction is added to the reaction system.

26. A process for producing an aromatic compound as claimed in claim 25, wherein said compound capable of trapping SO₂ is a compound selected from the group consisting of magnesium oxide, calcium oxide, zinc oxide, lithium oxide, sodium hydroxide, potassium hydroxide, calcium hydroxide, sodium carbonate, potassium carbonate, sodium silicate, triethylamine, tributylamine and trioctylamine.

27. A process for producing an aromatic compound as claimed in claim 25, wherein said compound capable of trapping SO₂ is used in an amount of 0.1 to 100 times by mol the amount of the aromatic sulfinic acid or a salt thereof.

28. A process for producing an aromatic compound as claimed in claim 7, wherein said salt of the aromatic sulfinic acid is a sodium salt.

29. A process for producing an aromatic compound as claimed in claim 1, wherein the halogen atom of the aromatic halogen compound or the vinyl group-containing halogen compound is a chlorine or bromine atom.

30. A process for producing an aromatic compound as claimed in claim 17, wherein said catalyst compound is a palladium salt of an organic acid and the organophosphorus compound ligand is 1,2-bis(diphenylphosphino)ethane or triphenylphosphine.

* * * * *